(12) United States Patent
Palushi et al.

(10) Patent No.: US 12,611,258 B2
(45) Date of Patent: Apr. 28, 2026

(54) REGISTRATION PROBE FOR ENHANCED INFORMATION CAPTURE

(71) Applicants: Acclarent, Inc., Irvine, CA (US);
Biosense Webster (Israel) Ltd.,
Yokneam (IL)

(72) Inventors: Jetmir Palushi, Irvine, CA (US);
Danielle N. Rossi, Mt. Laurel, NJ (US);
Helen Wolfson, Haifa (IL); Uriel Hod,
Haifa (IL); Itamar Bustan, Zichron
Ya'acov (IL)

(73) Assignees: Acclarent, Inc., Irvine, CA (US);
Biosense Webster (Israel) Ltd.,
Yokneam (IL)

( * ) Notice: Subject to any disclaimer, the term of this patent is extended or adjusted under 35 U.S.C. 154(b) by 993 days.

(21) Appl. No.: 17/325,256

(22) Filed: May 20, 2021

(65) Prior Publication Data

US 2022/0370143 A1 Nov. 24, 2022

(51) Int. Cl.
*A61B 34/20* (2016.01)
*A61B 34/00* (2016.01)

(52) U.S. Cl.
CPC .............. *A61B 34/20* (2016.02); *A61B 34/25*
(2016.02); *A61B 2034/2048* (2016.02); *A61B*
*2034/2051* (2016.02); *A61B 2034/2068*
(2016.02)

(58) Field of Classification Search
CPC .......... A61B 2017/00203; A61B 34/25; A61B
2034/2051; G06F 3/04883; G06F 1/1694;
G06F 3/017; G06F 3/0346
See application file for complete search history.

(56) References Cited

U.S. PATENT DOCUMENTS

| | | | |
|---|---|---|---|
| 7,225,131 B1 * | 5/2007 | Bangalore | G16H 15/00 |
| | | | 704/E15.045 |
| 7,720,521 B2 | 5/2010 | Chang et al. | |
| 7,889,928 B2 | 2/2011 | Shieh | |
| 8,447,611 B2 * | 5/2013 | Huang | G06F 16/686 |
| | | | 704/231 |
| 9,250,721 B2 * | 2/2016 | Mkrtchyan | G06F 3/03545 |
| 9,304,608 B2 * | 4/2016 | Tudosoiu | G06F 3/03545 |
| 10,409,955 B2 | 9/2019 | Apte et al. | |
| 10,444,868 B2 | 10/2019 | Lee | |
| 10,463,242 B2 | 11/2019 | Kesten et al. | |
| 10,561,370 B2 | 2/2020 | Salazar et al. | |
| 10,779,891 B2 | 9/2020 | Clopp | |
| 10,786,311 B2 | 9/2020 | Salazar et al. | |

(Continued)

FOREIGN PATENT DOCUMENTS

| | | | |
|---|---|---|---|
| WO | 20180189725 A1 | 10/2018 | |
| WO | 20200210782 A1 | 10/2020 | |

OTHER PUBLICATIONS

Rosenthal Et. al "A Voice-enabled, Structured Medical Reporting System", JAMIA, Nov.-Dec. 1997; 4(6): p. 436-441 (Year: 1997).*

*Primary Examiner* — Nyrobi Celestine
(74) *Attorney, Agent, or Firm* — Barnes & Thornburg LLP

(57) ABSTRACT

Tools used within a surgical area may be equipped with sensors that allow them to be tracked within the magnetic field of an image guided surgery (IGS) system. These tools may include a probe which is instrumented with a position sensor allowing it to be used not only for registration of non-magnetic objects within the magnetic field, but also for providing additional inputs.

13 Claims, 8 Drawing Sheets

(56)  References Cited

U.S. PATENT DOCUMENTS

| | | | |
|---|---|---|---|
| 2004/0034282 A1* | 2/2004 | Quaid, III | A61B 34/20 |
| | | | 600/300 |
| 2005/0054900 A1* | 3/2005 | Mawn | A61B 5/064 |
| | | | 600/156 |
| 2005/0113812 A1* | 5/2005 | Viswanathan | A61B 6/467 |
| | | | 606/1 |
| 2008/0118103 A1* | 5/2008 | Pescatore | A61B 34/20 |
| | | | 382/103 |
| 2008/0119712 A1* | 5/2008 | Lloyd | A61B 90/36 |
| | | | 600/407 |
| 2008/0319313 A1* | 12/2008 | Boivin | A61B 34/20 |
| | | | 600/424 |
| 2009/0080737 A1* | 3/2009 | Battle | A61M 25/0662 |
| | | | 382/131 |
| 2014/0275989 A1* | 9/2014 | Jacobsen | A61B 5/061 |
| | | | 600/424 |
| 2014/0364725 A1 | 12/2014 | Makower | |
| 2016/0008083 A1* | 1/2016 | Kesten | A61B 5/062 |
| | | | 600/424 |
| 2016/0054821 A1 | 2/2016 | Kim et al. | |
| 2017/0119473 A1* | 5/2017 | Clopp | A61M 29/02 |
| 2017/0135764 A1* | 5/2017 | Gliner | A61B 5/743 |
| 2019/0105072 A1* | 4/2019 | Govari | A61B 34/20 |
| 2019/0192228 A1* | 6/2019 | Salazar | A61B 90/13 |
| 2019/0299028 A1* | 10/2019 | Stopek | A61B 34/10 |
| 2020/0184661 A1* | 6/2020 | Amit | G06T 7/97 |
| 2020/0188031 A1* | 6/2020 | Palushi | A61B 5/062 |

* cited by examiner

700

702

TEXT

704

700

702

TEXT

704

REGISTRATION PROBE FOR ENHANCED INFORMATION CAPTURE

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While using an IGS system, relevant information may be captured using various conventional means, such as a keyboard, mouse, or touch screen interface. Such conventional means may be sufficient in some contexts. However, such conventional means may be less useful during a procedure, as a surgeon may have to leave the sterile room to interact with a keyboard and mouse, may have to relay voice commands to personnel at the keyboard and mouse, or may have to step away from or shift their focus from the patient to interact with a touchscreen within the sterile room. Each such interaction may require various additional steps in order to maintain sterility (e.g., re-sterilizing before returning to the sterile room, changing gloves after interacting with a touchscreen). Additionally, devices intended to be used within the sterile room may need to be specially prepared or specially manufactured so that they can resist contamination, allow for sterilization in between procedures, or be disposed after each procedure, any of which can impact the cost quality, and usability of such devices.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
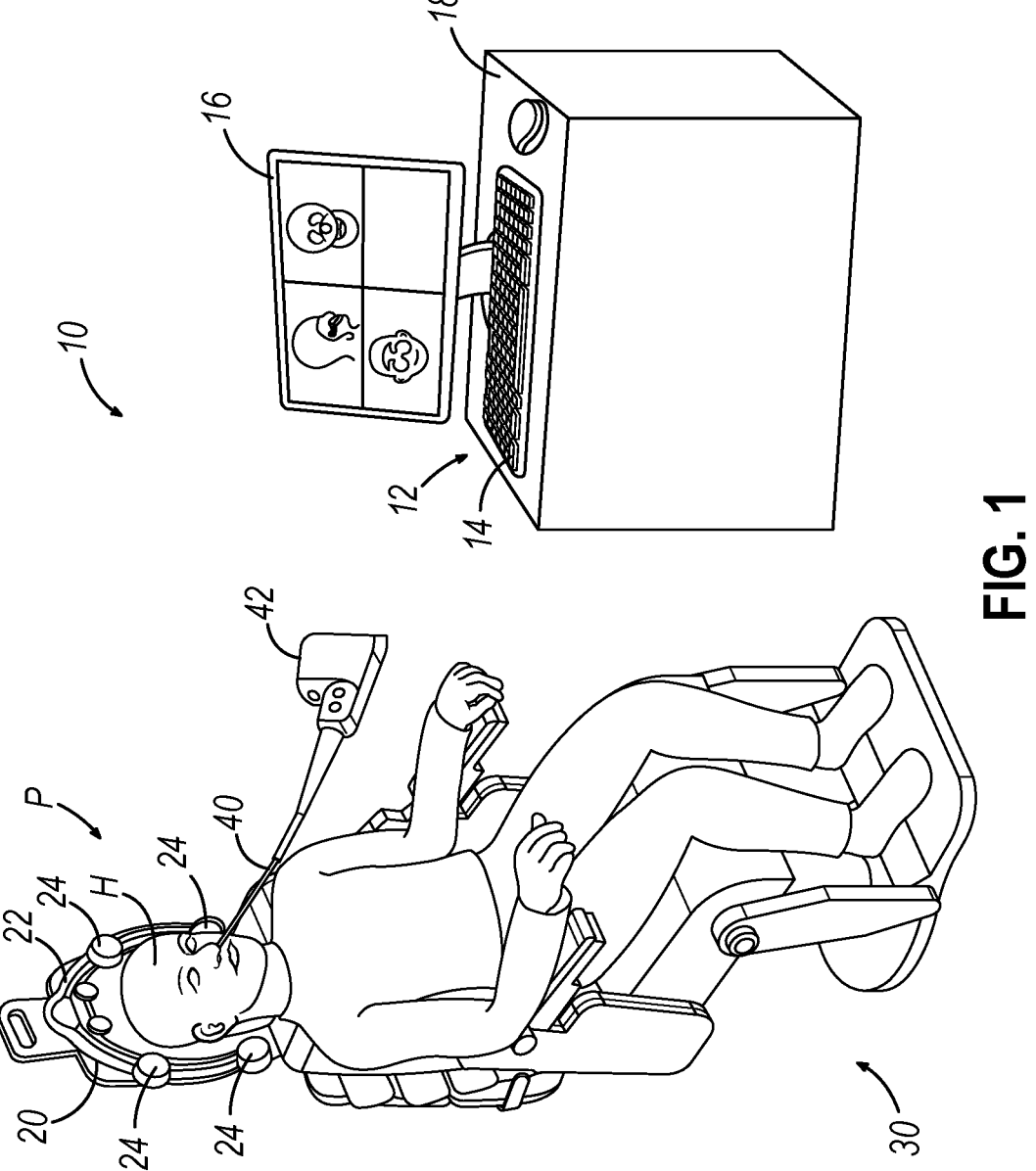
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the phrase "based on" is used to indicate that something is based at least in part upon something else. It will be further appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Exemplary Registration Probe with Space Tracking

While IGS navigation systems such as the IGS navigation system (10) may provide advantages during surgical procedures, conventional uses of such systems may be limited in some ways. In order to more fully leverage the power of an IGS navigation system (10), the localization functionality of the system may be used to support data capture, thereby providing improved benefits such as improved ease of use during a surgical procedure. For example, a standard computer mouse may be difficult to use in such a surgical environment because it may be difficult to find a contact surface for the optical or mechanical motion tracking element of such a device, and because a surgeon may be wearing gloves, or may have one or both hands already occupied with another tool or task. Similarly, computer keyboards may be difficult to manipulate when wearing sterile gloves, and may not be reusable, or may require cost increasing non-standard features allowing them to be used or reused within a sterile setting (e.g., covers or designs that eliminate areas where contamination can gather, specialized designs that can accommodate later sterilization procedures). Moreover, interacting with user input devices such as a mouse or keyboard may either require the operator to move back and forth between the patient and the user input device or require reliance on an assistant to interact with the user input device. Each of these scenarios may present inefficiencies or otherwise be undesirable.

Devices having features such as non-contact navigation (e.g., devices that, unlike an optical mouse, do not require a contact surface to function) and motion tracking navigation may provide advantages in ease of use during surgical procedures. Additionally, such functionality may also be advantageously integrated with tools and devices already used in surgical procedures, in order to introduce new functionality without introducing entirely new devices or tools.

Figure 2:
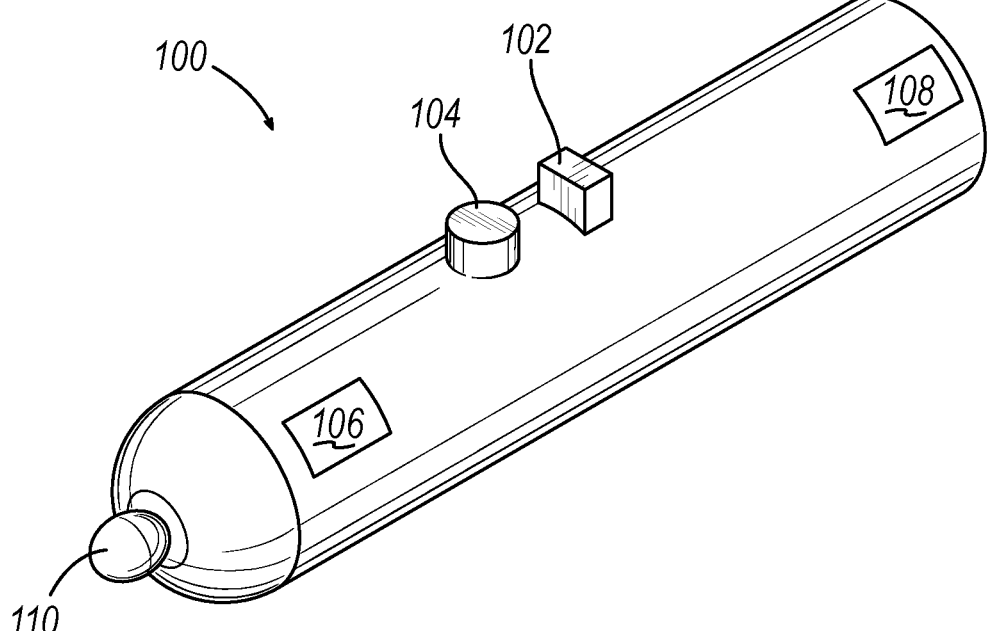
FIG. 2 depicts a perspective view of an exemplary registration probe usable with the surgery navigation system of FIG. 1.

For example, FIG. 2 shows a perspective view of an exemplary registration probe (100) usable with a surgery navigation system such as the IGS navigation system (10), that may be implemented having one or more features that aid in interactions with the IGS navigation system (10). A registration probe (100) may be used with some IGS techniques in order to register the location of various anatomical features of the patient (e.g., the location and orientation of anatomical landmarks on the patient's face) to the IGS navigation system (10) so that it can be correlated with the position of one or more tracked instruments. Examples of various forms that registration probe (100) may take, and registration functionalities that may be provided by registration probe (100), are described in U.S. Pat. No. 10,786,311, entitled "Apparatus and Method for Registering Facial Landmarks for Surgical Navigation System," issued Sep. 29, 2020, the disclosure of which is incorporated by reference herein; and U.S. Pat. No. 10,779,891, entitled "System and Method for Navigation of Surgical Instruments," issued Sep. 22, 2020, the disclosure of which is incorporated by reference herein. The following description provides additional ways in which a registration probe (100) may be used in a manner far beyond the conventional uses contemplated for a registration probe (100) as described in the above-noted references.

Figure 3:
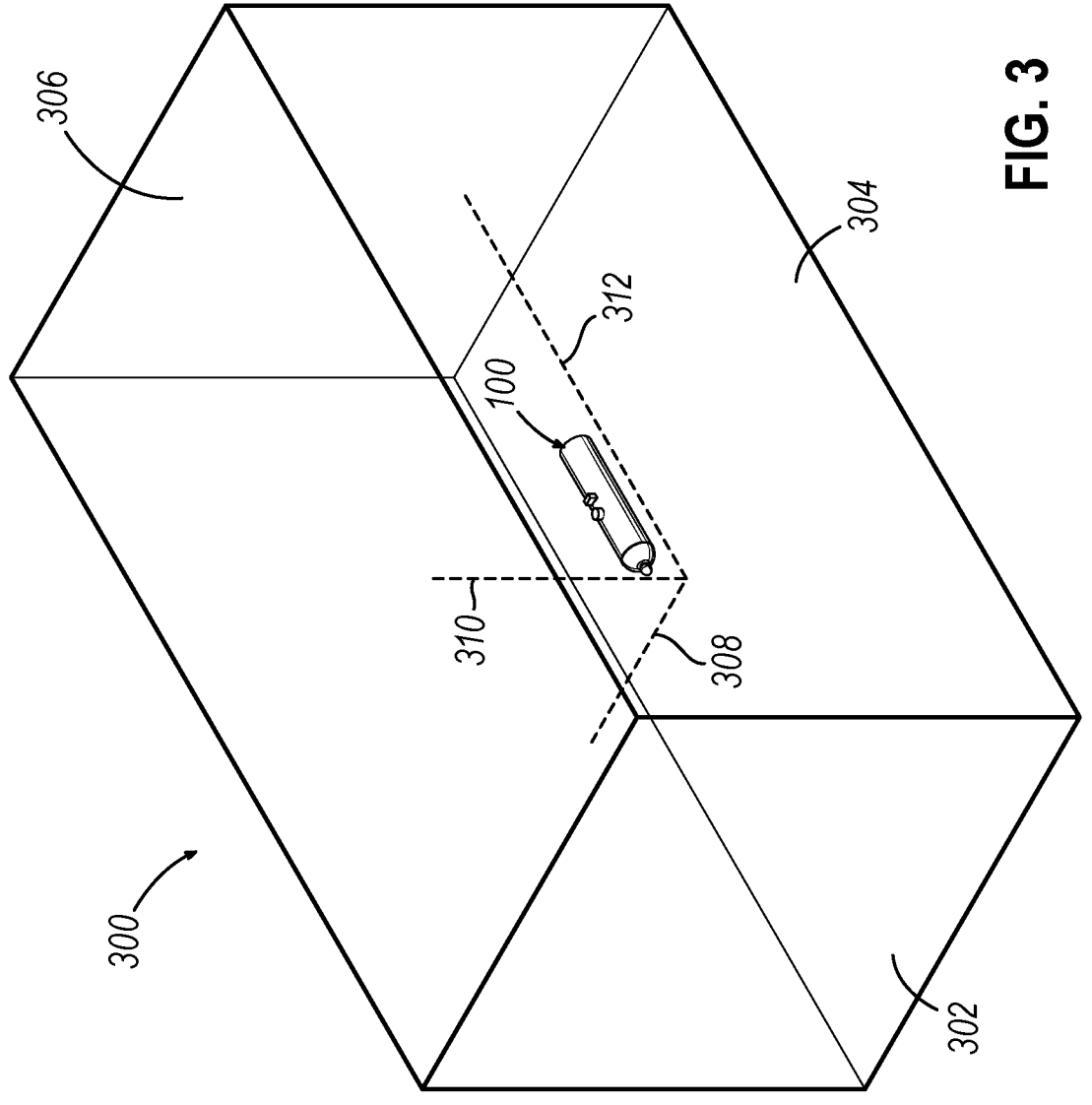
FIG. 3 depicts a diagram showing the registration probe of FIG. 2 being tracked within an exemplary tracked space by the surgery navigation system of FIG. 1.

The IGS navigation system (10) provides a tracked space (300) (e.g., an area in which the magnetic field sensors or other sensors can detect the positions and movements of surgical instruments having corresponding sensor elements, as shown in FIG. 3 and discussed in more detail below) in which the position of compatible devices can be tracked. This tracked space (300) is a three-dimensional space of varying sizes and shapes and may include at least the space in which the surgical procedure is performed (e.g., for a surgical procedure in or near paranasal sinuses, in a patient's head); but may also include additional portions of space beyond the particular surgical site (e.g., a space extending several feet in each direction from the patient's head).

While some instruments include elements or features that can be tracked within the tracked space (300), the position of a patient must also be known in order to provide accurate IGS navigation. Since a patient is not necessarily inherently trackable by the IGS navigation system (10), the registration probe (100) may be used to locate and register a surgical site, such as the patient's face, with the IGS navigation system (10) so that its position within the tracked space (300) may be determined. By determining the position of the patient's head (H) within the tracked space (300), IGS navigation system (10) may accurately correlate the location of anatomical structures in the patient's head (H) with anatomical structures represented by preoperatively obtained images (e.g., CT scans) and/or digital models, etc. of the patient's head (H) as already stored in IGS navigation system (10).

In some versions, the registration probe (100) includes a position sensor that is compatible with the IGS navigation system (10) and allows the registration probe (100) to be located within the tracked space (300); and also includes additional user inputs such as a first button (102), a second button (104), and a wireless transceiver (108). A patient may be registered by placing a tip (110) of the registration probe against a plurality of points across the patient's face and registering each point (e.g., manually by pressing a button such as the first button (102), or automatically where the tip (110) is configured to detect contact with the patient's face of a sufficient force to cause automatic registration). As each point is registered, a position sensor (e.g., as could be included in the tip (110)) provides that location, within the tracked space (300), to the IGS navigation system (10), which may use such information to correlate the position of any tracked surgical instruments with the patient's position.

While the registration probe (100) may be used to provide one or more features allowing a surgeon to capture information during a procedure, as will be described in more detail below, it should be understood that other surgical instruments that are trackable within the tracked space (300), or that are capable of independently providing signals indicating their position and movements (e.g., by use of accelerometers) and communicating such information to the IGS navigation system (10), may also be advantageously used as described herein. This may include, for example, positionally tracked guidewires, dilation instruments, shavers, endoscopes, cutting tools, and other surgical instruments as will be apparent to those skilled in the art in view of the teachings herein.

FIG. 3 shows a diagram showing a surgical instrument such as the registration probe (100) being tracked within the tracked space (300) by a surgery navigation system such as the IGS navigation system (10). While a tracked space may be of varying sizes and shapes, the tracked space (300) is depicted as being a three-dimensional rectangular space in which the registration probe (100) is contained. The registration probe (100) may be tracked in various ways within the tracked space (300) depending upon the capabilities of a particular IGS system and probe (e.g., number and location of position sensors). For example, in some implementations, the registration probe (100) may be tracked with three degrees of freedom (e.g., movement along an x, y, and z axis), while in others it may be tracked with six degrees of freedom (e.g., three degrees of freedom, as well as rotations about the x, y, and z axis). FIG. 3 shows the registration probe being tracked with three-degrees of freedom, represented by dotted lines, which include tracked movement along an x-axis (308), a y-axis (310), and a z-axis (312).

Such movements within the tracked space (300) may be interpreted by the IGS navigation system (10) as movements within the three-dimensional space therein; but may also be interpreted as movements within a two-dimensional area. When confining movements of the registration probe (100) to two dimensions, it can be seen that the tracked space (300) also includes a first canvas (302), which observes movements of the registration probe (100) along the x-axis (308) and y-axis (310); a second canvas (304), which observes movements along the y-axis (310) and z-axis (312); and a third canvas (306), which observes movements along the x-axis (308) and z-axis (312). Since IGS navigation system (10) or other computer system interfaces may be displayed in two-dimensions, interpreting movements of a tracked device such as the registration probe (10) in two dimensions (e.g., the first canvas (302)) may advantageously correspond to such IGS navigation system (10) or other computer system interfaces. As described below, this may be used for various purposes, such as cursor control of the type that could conventionally be provided by a computer mouse, or text input, such as could be provided by using paths traced using the registration probe (100) (e.g., on a first canvas (302)) as inputs to a handwriting recognition module.

Figures 6A, 6B:
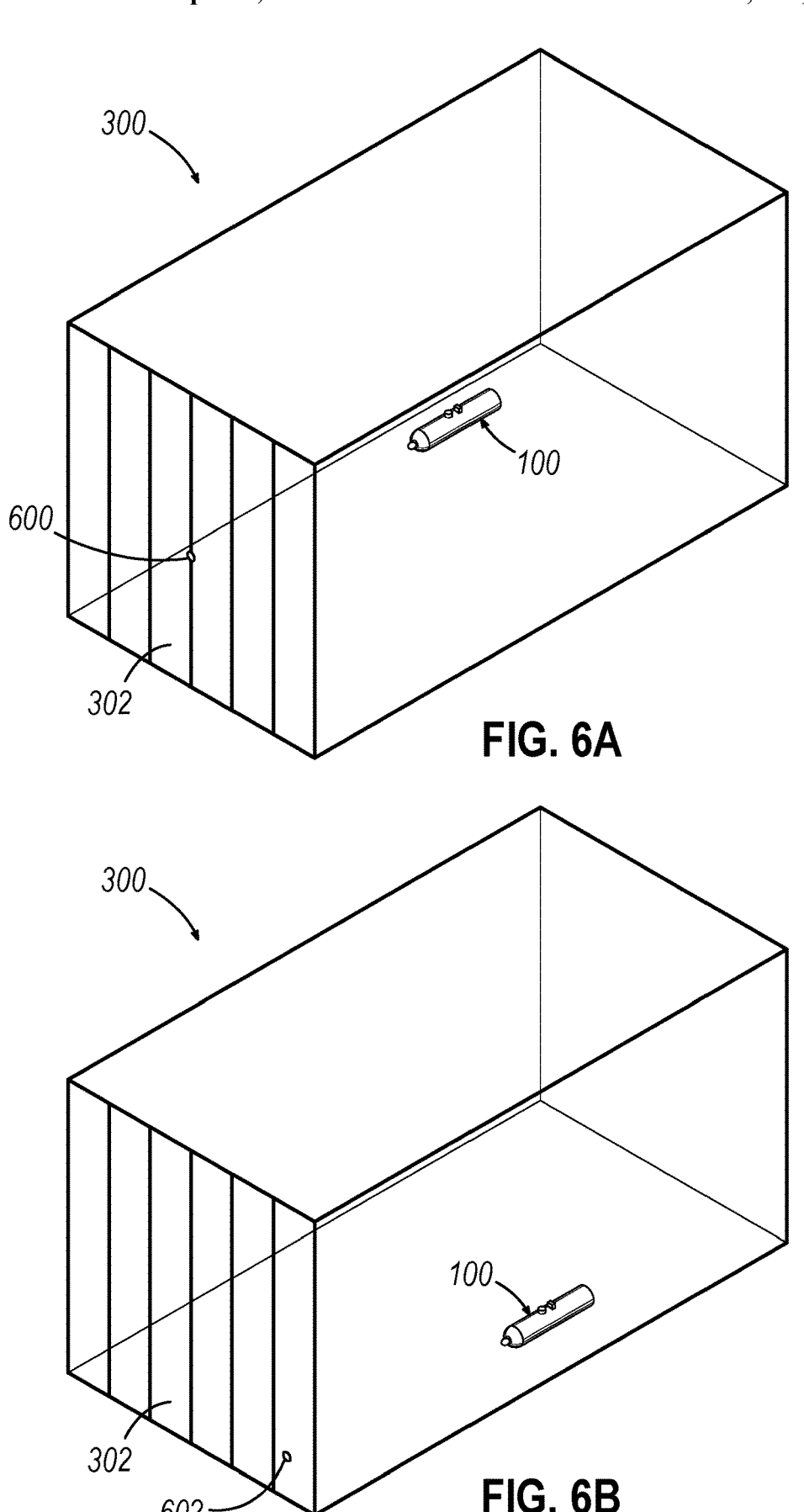
FIG. 6A depicts a diagram showing the position of the registration probe of FIG. 2 relative to a control canvas.
FIG. 6B depicts a diagram showing the position of the registration probe of FIG. 2 relative to the control canvas of FIG. 6A after a movement.
Figure 7A:
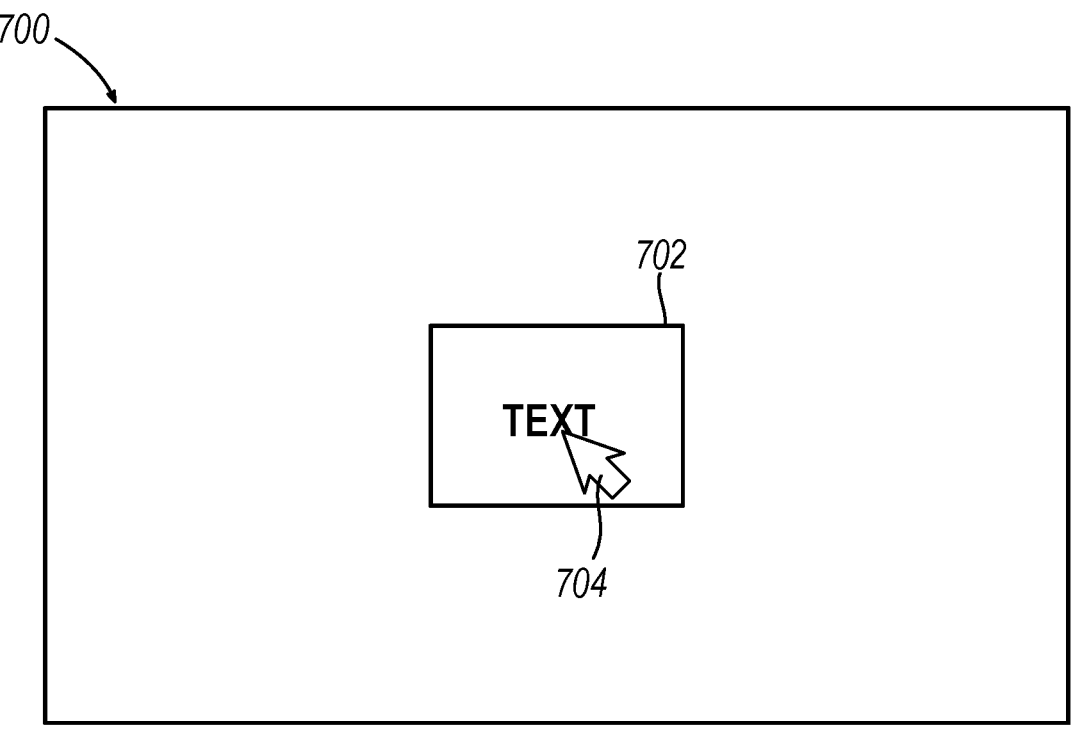
FIG. 7A depicts a screenshot of an exemplary image guided surgery (IGS) display associated with the arrangement shown in FIG. 6A.
Figure 7B:
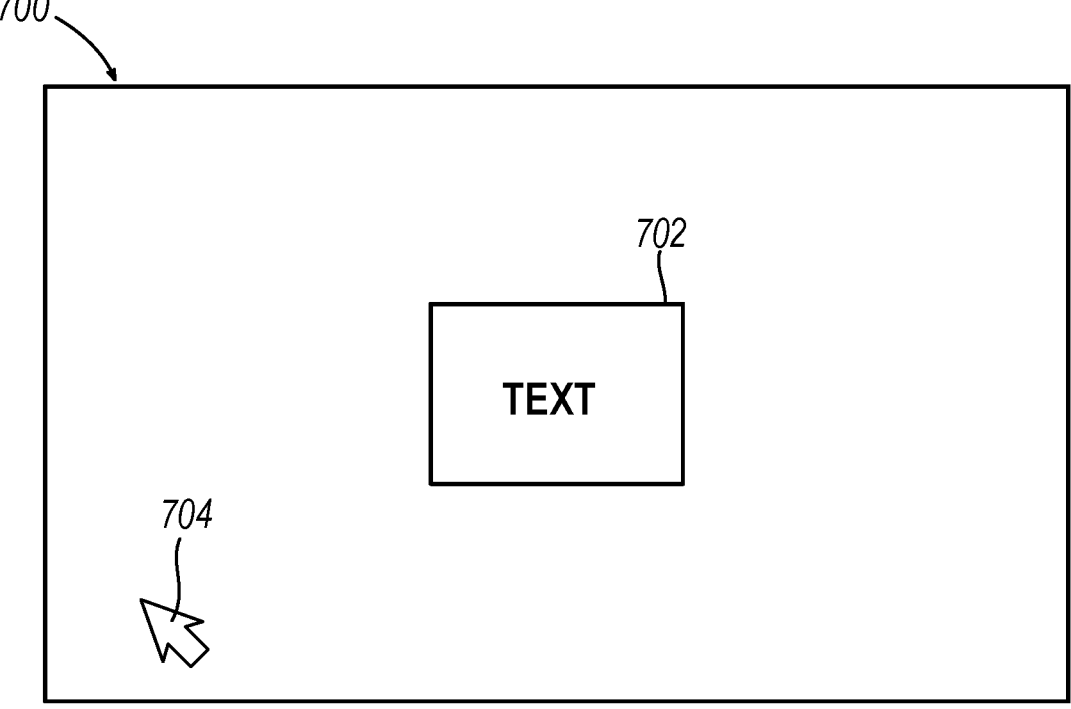
FIG. 7B depicts a screenshot of the IGS display associated with the arrangement shown in FIG. 6B.

To illustrate how a probe's movements in space may be used to provide inputs such as may otherwise be obtained by a mouse or other conventional control, FIGS. 6A and 6B each show the tracked space (300), with the registration probe's (100) position projected onto the first canvas (302), while FIGS. 7A and 7B show corresponding cursor positions on a display screen (16). As a note, when described herein as being projected onto a canvas, it should be understood that this is a descriptive term intended to aid in visualizing the movement of the registration probe (100) within the tracked space (300), relative to a specified viewpoint (e.g., the first canvas (302)). As such, the IGS navigation system (10) is not required to create corresponding software objects for canvases or projected points, or perform corresponding actions, though in some implementations it may do so. Similarly, the projection may or may not be configured such that the first canvas (or other two-dimensional space used to define the movements of the probe) would conform to any physical object. For example, in some implementations, the tracked space (300) may be oriented for purposes of input capture such that the first canvas (302) lays flat against the display screen (16) or against a wall of an operating theater (not pictured). However, this is not required and may not be present in all versions.

In FIG. 6A, the registration probe (100) is positioned at the approximate midpoint of the first canvas (302), as can be seen by the position (600) projected onto the first canvas (302). In FIG. 7A, the position (600) corresponds to the position of a cursor (704) in an interface (700) that may be displayed on the display screen (16) or another device. An interface element (702) may be readable text, an image, a clickable button or other control, or another similar feature that may be displayed to a user. In FIG. 6B, the registration probe (100) has been moved downwards and to the right within the tracked space (300), as can be seen by the position (602) projected onto the first canvas (302). In FIG. 7B, the position (602) corresponds to the position of the cursor (704), which has moved a direction and distance corresponding to the movement of the registration probe (100) within the tracked space (300). In this manner, it can be seen that the registration probe (100) can be used to control the movements of the cursor (704), in a manner that might otherwise require tools such as optical mice or keyboards that may not be suited to the surgical environment. Further since the registration probe (100), or another surgical instrument is already intended for use during a surgical procedure, it may provide such functionality without introducing an additional device or tool to the surgical area (e.g., as a stand-alone non-contact pointing device might) or requiring special implementation considerations (e.g., specially designing a mouse, keyboard, or other conventional input device to make it suitable for sterile procedure use and sterilization).

III. Exemplary Probe Input Methods

A. Note Taking

Figure 4:
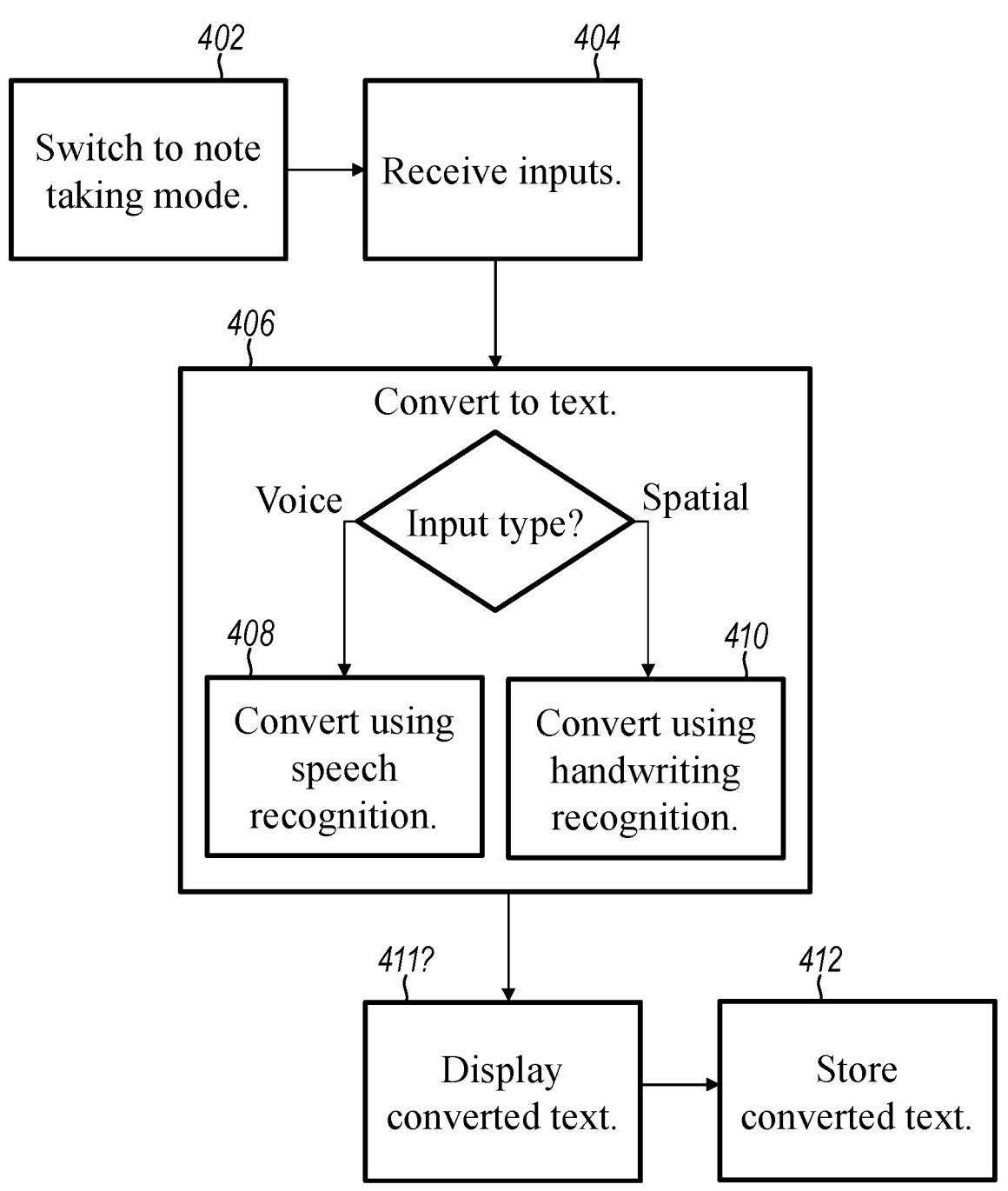
FIG. 4 depicts an exemplary set of high level steps that may be performed using the registration probe of FIG. 2.

As an example of a method in which a registration probe (100) is used for input, FIG. 4 depicts an exemplary set of high-level steps for note taking using a registration probe (100). Initially in a method such as shown in FIG. 4, a registration probe (100) will be switched (402) into note taking mode. This may be done, for example, by actuating a button (e.g., second button (104)) on the registration probe (100) after registration of the patient's position in three-dimensional space has been completed. In some versions, this may cause a signal to be sent from the registration probe (100) which would cause the processor (12) of the IGS navigation system (10) to display a note taking application on the display screen (16).

When in note taking mode, the IGS navigation system (10) could receive (404) inputs from the registration probe (100). This could be done, for example, by receiving location and orientation information from the registration probe and projecting a line from the tip of the probe to a virtual surface such as the first canvas (302), as previously described in the context of FIGS. 3, 6A, 6B, 7A and 7B. Alternatively, in some versions, this may be done by receiving speech input, such as could be captured by a microphone (106) included in the registration probe (100). Whether input is received (404) in the form of location and orientation information or speech information may vary between versions (e.g., some versions may be configured to capture input in the form of location and orientation information, while other versions may be configured to capture input in the form of speech). However, it is also possible that some versions may be configured to receive input (404) in the form of both speech and location/orientation information. For example, in some versions, if a user actuates the first button (102) then input may be captured in the form of speech (e.g., if the user speaks while holding down the first button (102), or if the user speaks after using the first button to turn on speech mode (102) but before using first button (102) to turn off speech mode, etc.), while if the user actuates the second button (104) then input may be captured in the form of position and orientation information. Other variations (e.g., a variation in which input can be captured in multiple manners that starts in a default input capture mode and cycles through other input capture modes based on button presses) are also possible, and will be immediately apparent to and could be implemented without undue experimentation by, those of ordinary skill in the art in light of this disclosure. Accordingly, the above description of various manners for receiving input (404) should be understood as being illustrative only, and should not be treated as limiting.

After the user's input has been received (404), it would be converted (406) into text. Just as inputs may be received (404) in a variety of manners, the conversion (406) of those inputs into text may take place in a variety of manners. For example, when input is received (404) in the form of position and location information, the conversion (406) of that input to text may include using the location and orientation information to project a location onto a first canvas (302), buffering locations on the first canvas (302) reflecting changes in location and/or orientation over time, and converting (310) patterns created by the buffered locations into text using handwriting recognition software. Similarly, when input is received (404) in the form of speech, the input may converted (408) to text using speech recognition software.

After the input is converted (406) to text, the text could be displayed (410), such in a window displayed by a note taking application, and stored (412), such as in memory comprised by the IGS navigation system (10). Additionally, in some implementations this storage (412) of text may be accompanied by storage of additional information related to the text. For example, in some implementations, converted text may be stored with temporal information (e.g., timestamps) indicating when the underlying input was received (404). This could later be used to correlate specific text with specific parts of the procedure, so that notes could effectively function as annotations in the event a user was reviewing a replay of endoscopic images captured during the procedure. As another example, in some cases converted text may be stored along with copies of the original input, so that if there was an error in the conversion process, the original input could be used as a reference for later disambiguation or correction. Other variations, such as combinations storing both original input and temporal information, are also possible, and will be immediately apparent to and could be implemented without undue experimentation by, those of ordinary skill in the art in light of this disclosure. Accordingly, the above examples should be understood as being illustrative only, and should not be treated as limiting.

B. Screen Markup

Figure 5:
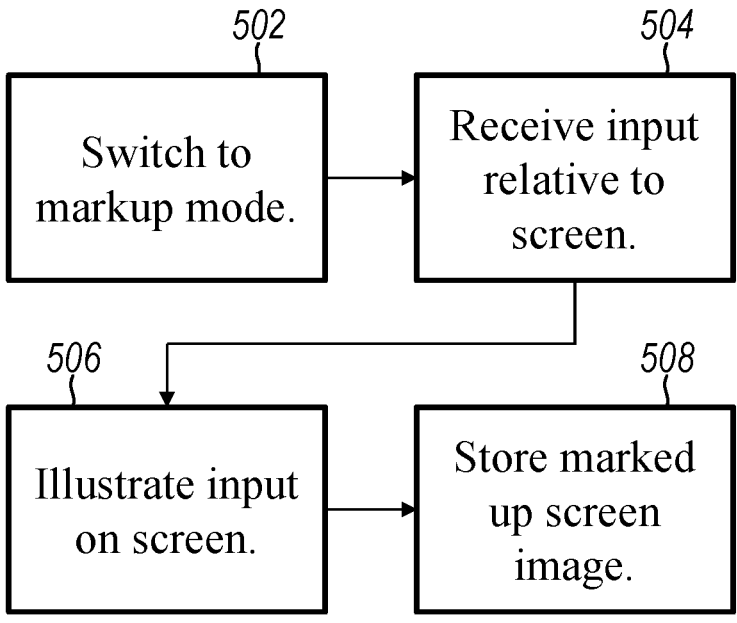
FIG. 5 depicts an exemplary set of high level steps that may be performed using the registration probe of FIG. 2.

Other methods in which a registration probe (100) is used for input are also possible. For example, FIG. 5 depicts a method in which a registration probe (100) is used to write on, paint or otherwise add information to a screen. In the method of FIG. 5, a registration probe (100) would initially be switched (502) into markup mode. This may be done in manners similar to those described above in the context of FIG. 4, such as actuating a button on the registration probe (100) that would cause a signal to be sent to the IGS navigation system (10) indicating that the user wished to use the registration probe (100) to mark up images on the IGS navigation system's display screen (16).

In response to the switch (502) to markup mode, the IGS navigation system (10) may treat position and orientation information it receives (504) from the registration probe as input relative to its display screen (16). This may be done, for example, by treating the registration probe (100) as existing in a tracked space (300) in which the first canvas (302) is coincident with the display screen (16) (e.g., by mapping a default coordinate system for the tracked space (300) onto a coordinate system in which the display screen (16) was coincident with the first canvas (302)). This may include steps in which the registration probe would be used to register the display screen (16) in the tracked space in a manner similar to the registration of a patient's body as described above. The orientation and location of the registration probe (100) as detected by the IGS navigation system (10) could then be used to project a ray from the tip of the registration probe which would be treated as defining the user's input at the point where the ray intersected the first canvas (302). This may be achieved in a variety of manners. For example, in some cases, this ray may be projected at an orientation which is coincident with the orientation of the probe's major axis in the tracked space (300), while in other cases, the tip of the probe in a two-dimensional plana parallel to the first canvas (302) may be projected directly onto the first canvas (302), essentially flattening any three-dimensional motion the probe may experience. Similarly, in some cases, an IGS navigation system (10) may further require that the user perform some additional action, such as actuating a first button (102) or a second button (104) while moving the registration probe (100) for the location and orientation information to be treated as defining input relative to the display screen (16).

After it is received (504), the user's input could be illustrated (506) on the display screen (16) in the same way if the user had provided input to a drawing program using a tool such as a light pen. This could then be stored (508) in a memory of the IGS navigation system (10), such as in connection with whatever image(s) were on the display screen at the time the user's input was received (504), so that the user could later retrieve the images marked up with whatever input he or she had provided. This could be used for a variety of purposes, such as surgical pre-planning, or in conjunction with note taking (e.g., where notes and screen markup may be coordinated via timestamps) as described previously.

C. Voice Commands and Other Variations

It should be understood that the above examples of a registration probe (100) and that other variations, either on the registration probe (100), its uses, or both, will be immediately apparent to, and could be implemented without undue experimentation by, those of ordinary skill in the art in light of this disclosure. For example, while the description accompanying FIG. 4 described how a microphone (106) may be used to provide spoken input that would be converted (408) into textual notes via speech recognition, it is also possible that a microphone (106) comprised by a registration probe (100) may be used for other purposes, such as providing spoken commands for controlling the IGS navigation system (10) during a procedure (e.g., if the registration probe (100) was switched to a voice command mode, such as through actuation of buttons as described previously). Additionally, in some versions providing such functionality, a IGS navigation system (10) may be configured with software which would automatically capture such spoken commands and incorporate them into a report following a procedure's conclusion.

Figure 8:
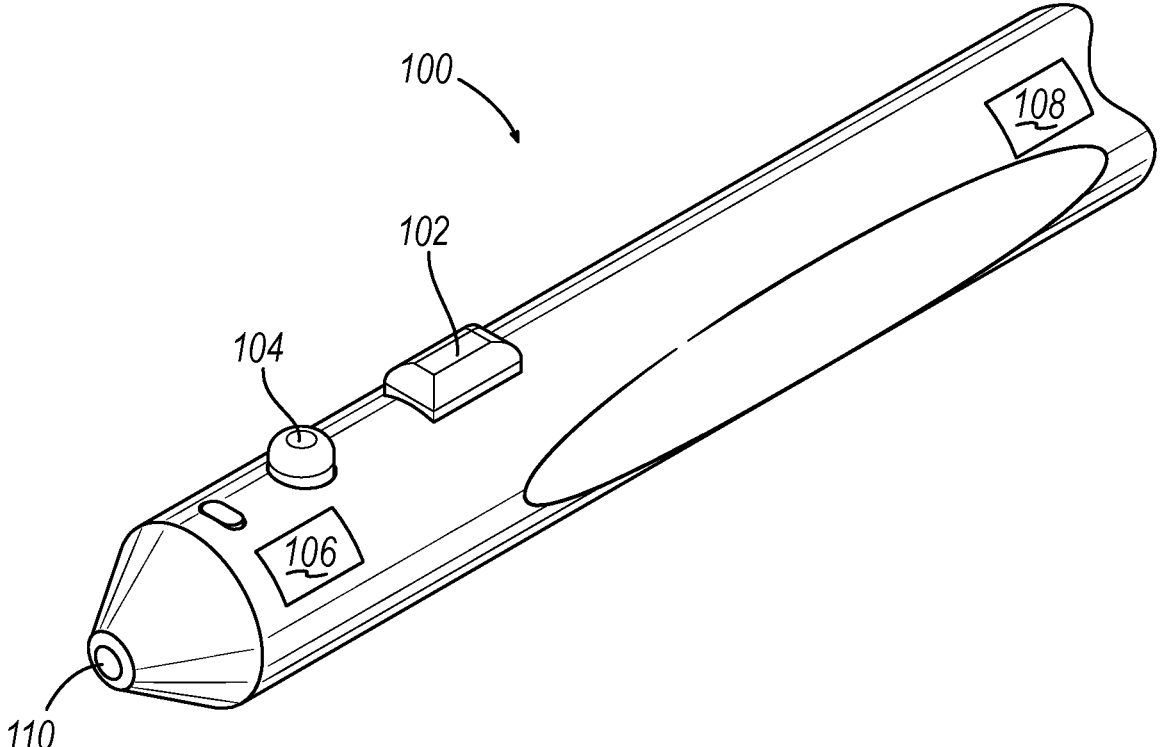
FIG. 8 depicts another exemplary registration probe usable with the surgery navigation system of FIG. 1.

Variations in form are also possible. For example, while FIG. 2 illustrated a potential form factor for a registration probe (100), other implementations are also possible, such as the alternate design illustrated in FIG. 8. Similarly, while FIGS. 2 and 8 illustrate forms for a registration probe (100) which include a first button (102) and a second button (104) which a user could actuate to control interactions with the IGS navigation system (10), it is possible that the disclosed technology may be implemented using a registration probe which includes more, or fewer, buttons than shown in FIGS.

2 and 8. For instance, a registration probe (100) may be implemented to include additional buttons, which buttons may correspond to additional modes of operation that a user could select, or which may correspond to specific actions that a user could perform (e.g., centering a cursor on a window in a display screen (16). Similarly, a registration probe (100) may be implemented with fewer or no buttons, and software on the IGS navigation system (10) could allow users to perform actions or switch between types of actions that could be performed using gesture control or similar input types. As another example, in some implementations, a registration probe (100) with a touch sensor implemented in its tip (110) may allow a user to mark up a screen display (16) by using touch signals from the registration probe (100) to indicate that movements detected by the IGS navigation system (10) should be treated as providing inputs (e.g., screen markup).

In view of the foregoing, it should be understood that a registration probe (100) may be used in a variety of different ways different ways during a procedure. This can include using the registration probe (100) in the pre-operative stage to register anatomical landmarks on a patient's head (H) with the IGS navigation system (10), thereby enabling the IGS navigation system (10) to correlate preoperatively obtained images or digital models of the patient's head (H) with the actual location of the patient's head (H) in a tracked space (300). It may also include capturing notes, marking up displays, or providing voice commands, depending on the functionality the probe is configured with or, in cases where a probe is configured with multiple potentially overlapping functions (e.g., a case where spoken input may be used for notes or voice commands), the mode a user has indicated for the probe. This may be much more convenient and efficient for the surgeon, as it allows the surgeon to avoid interacting with a keyboard or mouse. Moreover, the registration probe (100) may be placed on the patient's chest or some other location that is conveniently accessible to the surgeon.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of using an image guided surgery (IGS) navigation system, the method comprising: activating a tracking field generator comprising a set of magnetic field generators operable to produce a magnetic field defining a tracked area comprising a head of a subject; using a probe comprising a position sensor to measure a plurality of magnetic field positions on the head of the subject; generating a registration between the head of the subject and an image of the head of the subject based on the measurement of the plurality of magnetic field positions on the head of the subject; putting the IGS navigation system into an input mode using a control on the probe; and while the IGS navigation system is in the input mode, using the probe to capture an input from a user.

Example 2

The method of Example 1, wherein the method comprises: generating text based on the input from the user; displaying the text on an interface of a note taking application; and storing the text in a memory of the IGS navigation system.

Example 3

The method Example 2, wherein generating text based on the input from the user comprises: generating an input pattern by performing steps comprising buffering the input from the user; and providing the input pattern to a handwriting recognition program.

Example 4

The method of Example 2, wherein the input from the user is spoken input captured by a microphone comprised by the probe; and generating text based on the input from the user comprises providing the spoken input to a speech recognition program.

Example 5

The method of any of Examples 2 through 4, wherein storing the text in the memory of the IGS navigation system comprises storing the text with a timestamp corresponding to a time for the input from the user.

Example 6

The method of any of Examples 2 through 5, wherein: the input mode is a note taking mode; and the method comprises: receiving a signal from the probe indicating actuation of a button comprised by the probe; and automatically putting the IGS navigation system into the note taking mode and activating the note taking application based on receiving the signal from the probe.

Example 7

The method of Example 1, wherein: using the probe to capture the input from the user comprises defining a pattern based on movement of an intersection of a ray extending from a tip of the probe to a plane in the tracked area defined by the magnetic field; and the method comprises displaying the pattern on a display of the IGS navigation system.

Example 8

The method of Example 7, wherein the method comprises: using the probe to measure a plurality of magnetic field positions on the display of the IGS navigation system; and generating a registration between the display of the IGS navigation system and the plane in the tracked area based on the measurement of the plurality of magnetic field positions on the display of the IGS navigation system.

Example 9

The method of any of Examples 7 through 8, wherein displaying the pattern on the display of the IGS navigation system comprises displaying the pattern overlaid on an image of an interior of the subject during pre-operative planning.

Example 10

The method of any of Examples 7 through 8, wherein displaying the pattern on the display of the IGS navigation system comprises displaying the pattern overlaid on a real time image of an interior of the subject during a procedure.

Example 11

The method of any of Examples 7 through 10, wherein the ray extending from the tip of the probe to the plane in the tracked area is a ray extending an axis of the probe defined based on an orientation of the probe in the tracked area.

Example 12

The method of any of Examples 1 through 11, wherein the IGS navigation system is configured to switch between a first input mode and a second input mode based on user actuation of one or more buttons on the probe.

Example 13

The method of any of Examples 1 or 12, wherein: the input captured using the probe comprises a voice command; and the method comprises automatically: converting the voice command to text; and incorporating the text into a report of a procedure performed on the subject.

Example 14

The method of any of Examples 1 through 13, wherein: the probe comprises a first button, a second button, and a microphone; and the IGS navigation system is configured to: when the first button is depressed, treat movements of the probe within the tracked area as the input; and when the second button is depressed, treat sound captured by the microphone as the input.

Example 15

An image guided surgery (IGS) navigation system comprising: a probe comprising a position sensor; a tracking field generator operable to provide a tracked area, wherein the tracked area is a three dimensional space; a processor configured to: determine a position of the probe within the tracked area based upon a set of tracking data, wherein the set of tracking data is based on signals from the position sensor received by the processor as a result of an interaction of the probe with the tracked area; generate a registration between a head of a subject and an image of the head of the subject based on measurements from the probe of a plurality of magnetic field positions of the head of the subject; switching to an input mode based on a control signal received from the probe; and while in the input mode, receiving an input signal from the probe.

Example 16

The IGS navigation system of Example 15, wherein the processor is configured to: generate text based on the input signal from the probe; launch a note taking application and display the text on an interface of the note taking application; and store the text in a memory comprised by the IGS navigation system.

Example 17

The IGS navigation system of Example 16, wherein the processor of the IGS navigation system is configured to generate text based on the input signal from the probe using a program selected from a group consisting of: a handwriting recognition program; and a speech recognition program.

Example 18

The IGS navigation system of any of Examples 16 through 17, wherein the processor is configured to, when storing the text in the memory, storing a timestamp corresponding to a time for the input signal in the memory comprised by the IGS navigation system.

Example 19

The IGS navigation system of any of Examples 15 through 18, wherein the processor is configured to display a pattern based on the input signal as an overlay of an image of the interior of the subject on a display comprised by the IGS navigation system.

Example 20

An IGS navigation system comprising: a probe comprising a position sensor, a microphone, a first button and a second button; a tracking field generator operable to provide a tracked area, wherein the tracked area is a three dimensional space; a processor configured to: determine a position of the probe within the tracked area based upon a set of tracking data, wherein the set of tracking data is based on signals from the position sensor received by the processor as a result of an interaction of the probe with the tracked area; generate a registration between a head of a subject an image of the head of the subject based on measurements from the probe of a plurality of magnetic field positions of the head of the subject; receive a first signal indicating that the first button is depressed, and a second signal indicating that the second button is depressed; when the registration has been generated and the first button is depressed, treat movements of the probe within the tracked area of the magnetic tracking system as input from a user of the probe; and when the registration has been generated and the second button is depressed, treat sound captured by the microphone as input from the user of the probe.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using an image guided surgery (IGS) navigation system in the performance of a surgical procedure, the method comprising:
    (a) activating a tracking field generator comprising a set of magnetic field generators operable to produce a magnetic field defining a tracked space comprising a head of a subject;
    (b) using a probe comprising a position sensor to measure, within the magnetic field, a plurality of magnetic field positions on the head of the subject;
    (c) generating a registration between the head of the subject and an image of the head of the subject based on the measurement of the plurality of magnetic field positions on the head of the subject;
    (d) using the probe to measure a plurality of magnetic field positions on a display of the IGS navigation system;
    (e) generating a registration between the display of the IGS navigation system and a plane in the tracked space based on the measurement of the plurality of magnetic field positions on the display of the IGS navigation system, wherein the registration maps a default coordinate system for the tracked space to a first coordinate system in which the plane is coincident with the display of the IGS navigation system;
    (f) putting the IGS navigation system into an input mode using a control on the probe, wherein the control comprises a button, a switch, a microphone, or a sensor sensing a gesture performed by a user; and
    (g) while the IGS navigation system is in the input mode, using the probe to capture an input from the user, wherein the input is indicative of information provided by the user pertaining to the surgical procedure and is captured based on movement of an intersection of a ray extending from a tip of the probe to the plane in the tracked space defined by the magnetic field while the probe is in the magnetic field, wherein the plane is coincident with the display of the IGS navigation system.

2. The method of claim 1, wherein the method comprises:
    (a) generating text based on the input from the user;
    (b) displaying the text on an interface of a note taking application; and
    (c) storing the text in a memory of the IGS navigation system.

3. The method of claim 2, wherein generating text based on the input from the user comprises:
    (i) generating an input pattern by performing steps comprising buffering the input from the user, and1
    (ii) providing the input pattern to a handwriting recognition program.

4. The method of claim 2, wherein:
    (a) the input from the user additionally includes spoken input captured by a microphone comprised by the probe; and
    (b) generating text based on the input from the user comprises providing the spoken input to a speech recognition program.

5. The method of claim 2, wherein storing the text in the memory of the IGS navigation system comprises storing the text with a timestamp corresponding to a time for the input from the user.

6. The method of claim 2, wherein:
    (a) the input mode is a note taking mode; and
    (b) the method comprises:
        (i) receiving a signal from the probe indicating actuation of a button comprised by the probe, and
        (ii) automatically putting the IGS navigation system into the note taking mode and activating the note taking application based on receiving the signal from the probe.

7. The method of claim 1, wherein the movement of the intersection of the ray to the plane defines a pattern, the method further comprising displaying the pattern on the display of the IGS navigation system.

8. The method of claim 7, wherein displaying the pattern on the display of the IGS navigation system comprises displaying the pattern overlaid on an image of an interior of the subject during pre-operative planning.

9. The method of claim 7, wherein displaying the pattern on the display of the IGS navigation system comprises displaying the pattern overlaid on a real time image of an interior of the subject during the surgical procedure.

10. The method of claim 1, wherein the ray extending from the tip of the probe to the plane in the tracked space is a ray extending along a major axis of the probe defined based on an orientation of the probe in the tracked space.

11. The method of claim 1, wherein the IGS navigation system is configured to switch between a first input mode and a second input mode based on user actuation of one or more buttons on the probe.

12. The method of claim 1, wherein:

(a) the input captured using the probe comprises a voice command; and (b) the method comprises automatically:

(i) converting the voice command to text, and (ii) incorporating the text into a report of a procedure performed on the subject.

13. The method of claim 1, wherein:

(a) the probe comprises a first button, a second button, and a microphone; and (b) the IGS navigation system is configured to:

(i) when the first button is depressed, treat movements of the probe within the tracked space as the input, and (ii) when the second button is depressed, treat sound captured by the microphone as the input.

\* \* \* \* \*